US007488846B2

(12) United States Patent
Hedvati et al.

(10) Patent No.: US 7,488,846 B2
(45) Date of Patent: Feb. 10, 2009

(54) PREGABALIN FREE OF LACTAM AND A PROCESS FOR PREPARATION THEREOF

(75) Inventors: Lilach Hedvati, Doar Na Hefer (IL); Gideon Pilarski, Holon (IL); Yuriy Raizi, Natanya (IL); Sharon Tomer, Tel Aviv (IL); Ziv Dee-Noor, Haifa (IL); Claude Singer, Kfar Saba (IL)

(73) Assignee: Teva Pharmaceuical Industries Ltd., Petah Tiqva (IL)

( * ) Notice: Subject to any disclaimer, the term of this patent is extended or adjusted under 35 U.S.C. 154(b) by 431 days.

(21) Appl. No.: 11/402,415

(22) Filed: Apr. 11, 2006

(65) Prior Publication Data

US 2006/0281816 A1 Dec. 14, 2006

Related U.S. Application Data

(60) Provisional application No. 60/735,069, filed on Nov. 8, 2005, provisional application No. 60/733,006, filed on Nov. 2, 2005, provisional application No. 60/689,699, filed on Jun. 9, 2005, provisional application No. 60/679,784, filed on May 10, 2005, provisional application No. 60/670,425, filed on Apr. 11, 2005.

(51) Int. Cl.
*C07C 227/00* (2006.01)
(52) U.S. Cl. .................................................. 562/554
(58) Field of Classification Search .................. None
See application file for complete search history.

(56) References Cited

U.S. PATENT DOCUMENTS

| | | | |
|---|---|---|---|
| 5,010,189 | A | 4/1991 | Herold et al. |
| 5,599,973 | A | 2/1997 | Silverman et al. |
| 5,616,793 | A | 4/1997 | Huckabee et al. |
| 5,629,447 | A * | 5/1997 | Huckabee et al. ........... 562/553 |
| 5,637,737 | A | 6/1997 | Andres et al. |
| 5,637,767 | A | 6/1997 | Grote et al. |
| 6,197,819 | B1 | 3/2001 | Silverman et al. |
| 6,333,198 | B1 | 12/2001 | Edmeades et al. |
| 6,488,964 | B2 * | 12/2002 | Bruna et al. ................. 424/490 |
| 6,891,059 | B2 | 5/2005 | Burk et al. |
| 6,924,377 | B2 | 8/2005 | Blazecka et al. |
| 7,141,695 | B2 | 11/2006 | Przewosny et al. |
| 2001/0016665 | A1 | 8/2001 | Grote et al. |
| 2002/0012679 | A1 | 1/2002 | Bruna et al. |
| 2003/0225149 | A1 | 12/2003 | Blazecka et al. |
| 2005/0222464 | A1 | 10/2005 | Hoge, II |
| 2005/0228190 | A1 | 10/2005 | Bao et al. |
| 2005/0283023 | A1 | 12/2005 | Hu et al. |
| 2006/0270871 | A1 | 11/2006 | Khanduri et al. |
| 2007/0073085 | A1 | 3/2007 | Hedvati et al. |
| 2008/0014280 | A1 | 1/2008 | Kumar et al. |

FOREIGN PATENT DOCUMENTS

| | | |
|---|---|---|
| CN | 1 634 869 | 7/2005 |
| CZ | 297 970 | 3/2007 |
| WO | WO 96/38405 | 12/1996 |
| WO | WO 96/40617 | 12/1996 |
| WO | WO 01/55090 A1 | 8/2001 |
| WO | WO 2005/100580 | 10/2005 |
| WO | WO 2006/000904 A2 | 1/2006 |
| WO | WO 2006/008640 | 1/2006 |
| WO | WO 2006/136087 | 12/2006 |
| WO | WO 2008/004044 | 1/2008 |
| WO | WO 2008/007145 | 1/2008 |
| WO | WO 2008/009897 | 1/2008 |

OTHER PUBLICATIONS

Andruszkiewicz and Silverman, "A Convenient Synthesis of 3-Alkyl-4-Aminobutanoic Acids," *Synthesis*, 953-955 (1989).
Barnes, D.M., et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).
Berner et al. "Asymmetric Michael Additions to Nitroalkenes," *European Journal of Organic Chemistry*, 1877-1894 (2002).
Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).
Chen, AO et al., "Synthesis of Pregabalin," *Zhongguo YiYao Gongye Zazhi*, 35(4): 195-196 (2004).
Colonge et al., "Preparation De Pyrrolidones-2 et de Gamma-Aminoacides," *Bulletin De La Societe Chimique De France, Societe Francaise De Chimie*, 598-603 (1962).
Day and Thorpe, "The Formation and Reactions of Imino-compounds. Part XX. The Condensation of Aldehydes with Cyanoacetamide," *J. Chem. Soc.*, 117: 1465-1474 (1920).
Hoekstra, M.S. et al., "Chemical Development of CI-1008, an Enantiomerically Pure Anticonvulsant," *Organic Process Research and Development*, 1(1): 26-38 (1997).
Karanewsky, D.S. et al., "Practical Synthesis of an Enantiomerically Pure Synthon for the Preparation of Mevinic Acid Analogues," *J. Org. Chem.*, 56(11): 3744-3747 (1991).
Li, H. et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).
Martin, L. et al., "Pregabalin," *Drugs of the Future*, 24(8): 862-870 (1999).
Okino, T. et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).

(Continued)

*Primary Examiner*—Karl J Puttlitz
(74) *Attorney, Agent, or Firm*—Kenyon & Kenyon LLP

(57) ABSTRACT

The present invention encompasses Pregabalin substantially free of Lactam and a process for obtaining Pregabalin substantially free of Lactam comprising extracting an acidic mixture containing a complex of Pregabalin with a strong mineral acid, with $C_{3\text{-}8}$ alcohol; and combining the organic phase with an organic base.

27 Claims, No Drawings

OTHER PUBLICATIONS

Sammis, G.M. et al., "Highly Enantioselective Catalytic Conjugate Addition of Cyanide to α, β-Unsaturated Imides", *J. Am. Chem. Soc.*, 125(15): 4442-43 (2003).

Shintani, Ryo et al., "Highly Enantioselective Desymmetrization of Anhydrides by Carbon Nucleophiles: Reactions of Grignard Reagents in the Presence of (−)-Sparteine," *Angewandte Chemie, International Edition*, 41(6): 1057-1059 (2002).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma, Rekha et al., "Desymmetrization of prochiral anhydrides with Evans' oxazolidinones: an efficient route to homochiral glutaric and adipic acid derivatives," *J. Chem. Soc., Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

Strobel et al., *Chemical Instrumentation: A Systematic Approach, 3rd Ed.*, (1989), pp. 391-393, 879-894, 922-925, 953, John Wiley & Sons, Inc.

Snyder et al., *Introduction To Modern Liquid Chromatography, 2nd Ed.*, (1979), pp. 549-572, John Wiley & Sons, Inc.

* cited by examiner

PREGABALIN FREE OF LACTAM AND A PROCESS FOR PREPARATION THEREOF

RELATED APPLICATIONS

This application claims the benefit of U.S. provisional application Nos. 60/733,006, filed Nov. 2, 2005; 60/735,069, filed Nov. 8, 2005; 60/670,425, filed Apr. 11, 2005; 60/679,784, filed May 10, 2005; and 0/689,699, filed Jun. 9, 2005 herein incorporated by reference.

FIELD OF INVENTION

The present invention relates to (S)-Pregabalin substantially free of lactam, and a process for preparation thereof.

BACKGROUND OF THE INVENTION (S)-Pregabalin, (S)-(+)-3-(aminomethyl)-5-methylhexanoic acid, a compound having the chemical structure,

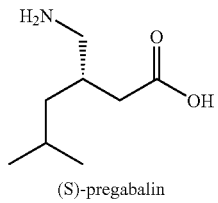

(S)-pregabalin is a γ-amino butyric acid or (S)-3-isobutyl (GABA) analogue. (S)-Pregabalin has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity. (S)-Pregabalin is marketed under the name Lyrica® by Pfizer, Inc.

Like any synthetic compound, (S)-Pregabalin can contain extraneous compounds or impurities that can come from many sources. They can be unreacted starting materials, by-products of the reaction, products of side reactions, or degradation products. Impurities in (S)-Pregabalin or any active pharmaceutical ingredient (API) are undesirable and, in extreme cases, might even be harmful to a patient being treated with a dosage form containing the API.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as (S)-pregabalin, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

As discussed above, (S)-Pregabalin can contain (S)-Lactam impurity of the following formula,

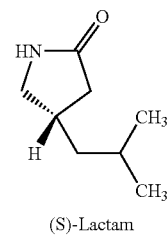

(S)-Lactam which is obtained by an intramolecular cyclization of (S)-Pregabalin under acidic conditions, as described by the following scheme:

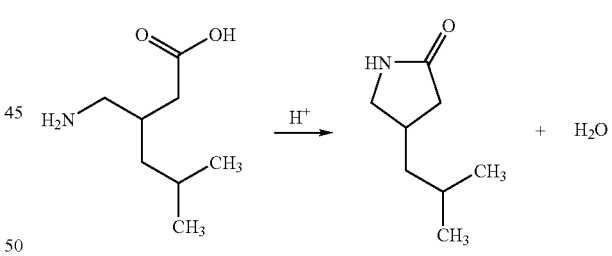

wherein the proton source can be an acid from the process or Pregabalin itself. Hence, (S)-Pregabalin obtained in any kind of process, will be contaminated with this impurity. However, the present invention succeeds to provide not only, (S)-Pregabalin substantially free of (S)-Lactam, but also, a process to obtain (S)-Pregabalin substantially free of (S)-Lactam.

Generally, side products, by-products, such as the Lactam, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position on the TLC plate and, wherein the position on the plate is measured in cm from the base line of the plate or by its relative position in the chromatogram of the HPLC, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. (Strobel p. 924, Snyder p. 549, Snyder, L. R.; Kirkland, J. J. Introduction to Modem Liquid Chromatography, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. (Strobel p. 894). For this purpose, the reference standard is added directly to the mixture, and is known as an "internal standard." (Strobel p. 925, Snyder p. 552).

The reference standard can serve as an internal standard when, without the deliberate addition of the reference standard, an unknown mixture contains a detectable amount of the reference standard compound using the technique known as "standard addition."

In the "standard addition technique", at least two samples are prepared by adding known and differing amounts of the internal standard. (Strobel pp. 391-393, Snyder pp. 571, 572). The proportion of the detector response due to the reference standard present in the mixture without the addition can be determined by plotting the detector response against the amount of the reference standard added to each of the samples, and extrapolating the plot to zero concentration of the reference standard. (See, e.g., Strobel, FIG. 11.4 p. 392). The response of a detector in HPLC (e.g. UV detectors or refractive index detectors) can be and typically is different for each compound eluting from the HPLC column. Response factors, as known, account for this difference in the response signal of the detector to different compounds eluting from the column.

As is known by those skilled in the art, the management of process impurities is greatly enhanced by understanding their chemical structures and synthetic pathways, and by identifying the parameters that influence the amount of impurities in the final product.

In this application the reference standard is the impurity (S)-Lactam in the API. Detection or quantification of the reference standard serves to establish the level of purity of the API. Use of a compound as a standard requires recourse to a sample of substantially pure compound.

SUMMARY OF THE INVENTION

In one embodiment, the present invention encompasses Pregabalin substantially free of Lactam.

In another embodiment, the present invention encompasses Pregabalin containing less than 0.015% area by HPLC of Lactam.

In yet another embodiment, the present invention encompasses a process for obtaining Pregabalin substantially free of Lactam by extracting an acidic mixture containing a complex of Pregabalin with a strong mineral acid, with a $C_{4-8}$ alcohol; and combining the organic phase with an organic base.

In another embodiment, the present invention encompasses a process for obtaining Pregabalin containing less than 0.005% area by HPLC of Lactam by extracting an acidic mixture containing a complex of Pregabalin with a strong mineral acid, with a $C_{4-8}$ alcohol; and combining the organic phase with an organic base.

In yet another embodiment, the present invention encompasses a process of determining the presence of a compound in a sample comprising carrying out HPLC or TLC with Lactam as a reference marker.

In one embodiment, the present invention encompasses a method of determining the relative retention time (RRT) of an impurity in a sample of Lactam comprising:
   a) measuring by HPLC or TLC the relative retention time (RRT) corresponding to Lactam in a reference marker sample;
   b) determining by HPLC or TLC the relative retention time (RRT) corresponding to Lactam in a sample comprising Lactam and Pregabalin; and
   c) determining the relative retention time (RRT) of Lactam in the sample by comparing the relative retention time (RRT) of step (a) to the relative retention time (RRT) of step (b).

In another embodiment, the present invention encompasses a process of determining the amount of a compound in a sample comprising carrying out HPLC or TLC with a Lactam as a reference standard.

In yet another embodiment, the present invention provides a method of determining the amount of an impurity in a sample of Lactam comprising:
   a) measuring by HPLC or TLC the area under a peak corresponding to Lactam in a reference standard comprising a known amount of Lactam;
   b) measuring by HPLC or TLC the area under a peak corresponding to Lactam in a sample comprising Lactam and Pregabalin; and
   c) determining the amount of Lactam in the sample by comparing the area of step (a) to the area of step (b).

In one embodiment, the present invention provides an HPLC method for used to determine the amount of Lactam in Pregabalin sample comprising combining a Pregabalin sample with a mixture of acetonitrile:methanol:buffer in a ratio of about 1:1:8, to obtain a solution; injecting the solution into a 250×4.6 mm Inertsil ODS 3V (or similar) column, followed by eluting the sample from the column at about 50 min using a mixture of acetonitrile:methanol:buffer (1:1:8) (referred to as eluent A) and acetonitrile (referred to as eluent B) as an eluent, and measuring the Lactam content in the relevant sample with a UV detector.

In another embodiment, the present invention provides pharmaceutical composition comprising (S)-Pregabalin substantially free of (S)-Lactam and non-acidic pharmaceutically acceptable excipients.

In yet another embodiment, the present invention provides a process for preparing pharmaceutical formulation comprising mixing (S)-Pregabalin substantially free of (S)-Lactam and a non-acidic pharmaceutically acceptable carrier.

In one embodiment, the present invention provides the use of the (S)-Pregabalin substantially free of (S)-Lactam of the present invention for the manufacture of a pharmaceutical composition.

DETAILED DESCRIPTION OF THE INVENTION

As used herein, unless specified otherwise, the term "Lactam" refers to either the S-enantiomer of the Lactam ((S)-Lactam) or to Lactam racemate (Lactam).

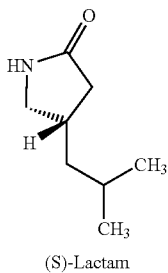
(S)-Lactam

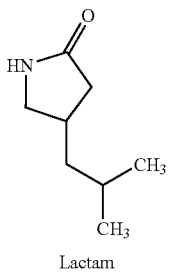
Lactam

As used herein, unless specified otherwise, the term "Pregabalin" refers to either the S-enantiomer of Pregabalin ((S)-Pregabalin) or to Pregabalin racemate.

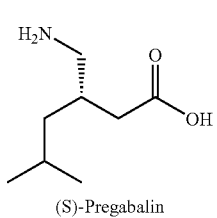
(S)-Pregabalin          Pregabalin

As used herein, unless specified otherwise, Pregabalin racemate contains lactam racemate.

As used herein, unless specified otherwise, (S)-Pregabalin contains (S)-lactam.

As used herein, unless specified otherwise, the term "CMH" refers to either the R-enantiomer of CMH ((R)—CMH) or to CMH racemate.

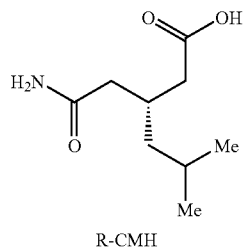
R-CMH

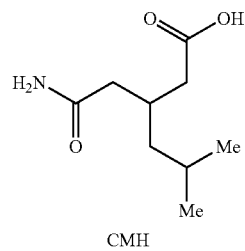
CMH

As used herein, the term "substantially free of Lactam" refers to Pregabalin containing less than 0.02% area by HPLC of Lactam.

The present invention provides Pregabalin substantially free of Lactam.

The present invention provides Pregabalin containing less than 0.015% area by HPLC of Lactam, preferably, less than 0.01% area by HPLC of Lactam, and more preferably, less than 0.005% area by HPLC of Lactam.

The present invention further provides a process for obtaining Pregabalin substantially free of Lactam by extracting an acidic mixture containing a complex of Pregabalin with a strong mineral acid, with a $C_{4-8}$ alcohol; and combining the organic phase with an organic base.

Preferably, the strong mineral acid is selected from the group consisting of: HCl, HBr, $H_3PO_4$, and $H_2SO_4$. More preferably, the strong mineral acid is $H_2SO_4$. At the end of the process, the Lactam remains soluble in the mixture of solvents. Preferably, at the end of the process a precipitate of Pregabalin is obtained. The precipitate of Pregabalin may be recovered by cooling, filtering and drying in a vacuum oven.

The complex of Pregabalin with a strong mineral acid may be prepared according to any process known to one skilled in the art or according to the process disclosed in U.S. Provisional Application Ser. No. 60/679,784, by reacting CMH with bromine, in a Hoffman reaction, under basic conditions, at a temperature of about 60° C. to about 85° C., to obtain a basic mixture. The basic mixture is then combined with a strong mineral acid, to obtain an acidic mixture containing a complex of Pregabalin with the strong mineral acid.

Preferably, Pregabalin obtained by the above process is substantially free of Lactam.

A preferred $C_{3-8}$ alcohol is butanol, iso-butanol, 2-butanol, iso-propyl alcohol, pentanol or iso-pentanol. The more preferred $C_{3-8}$ alcohol is iso-butanol.

Preferably, the organic base is selected from the group consisting of: primary amine, secondary amine, tertiary amine and aromatic amine. Preferably, the primary amine, secondary amine and tertiary amine are one of $C_1$ to $C_6$ alkyl amine, more preferably $C_1$ to $C_4$ alkylamine. Preferably, the aromatic amine is pyridine. The more preferred amine is either secondary amine or tertiary amine, more preferably, either secondary $C_1$ to $C_6$ alkyl amine or tertiary $C_1$ to $C_6$ alkyl amine, more preferably, either secondary $C_1$ to $C_4$ alkylamine or tertiary $C_1$ to $C_4$ alkylamine and most preferably, tertiary $C_1$ to $C_4$ alkylamine. Preferably, the secondary $C_1$ to $C_4$ alkylamine is either diisopropylamine or dipropylamine. Preferably, the tertiary $C_1$ to $C_4$ alkylamine is tributyl amine or triethyl amine. More preferably, the tertiary $C_1$ to $C_4$ alkylamine is tributyl amine.

The present invention provides a process of determining the presence of a compound in a sample comprising carrying out HPLC or TLC with Lactam as a reference marker.

The present invention further provides a method of determining the relative retention time (RRT) of an impurity in a sample of Lactam comprising:

a) measuring by HPLC or TLC the relative retention time (RRT) corresponding to Lactam in a reference marker sample;
b) determining by HPLC or TLC the relative retention time (RRT) corresponding to Lactam in a sample comprising Lactam and Pregabalin; and
c) determining the relative retention time (RRT) of Lactam in the sample by comparing the relative retention time (RRT) of step (a) to the relative retention time (RRT) of step (b).

The present invention provides a process of determining the amount of a compound in a sample comprising carrying out HPLC or TLC with a Lactam as a reference standard.

The present invention provides a method of determining the amount of an impurity in a sample of Lactam comprising:
a) measuring by HPLC or TLC the area under a peak corresponding to Lactam in a reference standard comprising a known amount of Lactam;
b) measuring by HPLC or TLC the area under a peak corresponding to Lactam in a sample comprising Lactam and Pregabalin; and
c) determining the amount of Lactam in the sample by comparing the area of step (a) to the area of step (b).

The present invention provides an HPLC method used to determine the presence of Lactam in Pregabalin sample comprising combining a Pregabalin sample with a mixture of acetonitrile:methanol:buffer in a ratio of about 1:1:8, to obtain a solution. The obtained solution is then injected into a 250×4.6 mm Inertsil ODS 3V (or similar) column, followed by eluting the sample from the column at about 50 min using a mixture of acetonitrile:methanol:buffer (1:1:8) (referred to as eluent A) and acetonitrile (referred to as eluent B) as an eluent, and measuring the Lactam content in the relevant sample with a UV detector (preferably at a 210 nm wavelength).

Preferably, the buffer contains $H_3PO_4$ and an aqueous solution of $(NH_4)_2HPO_4$ in a concentration of about 0.04M having a pH of about 6.5.

Preferably, the eluent used may be a mixture of eluent A and eluent B, wherein the ratio of them varies over the time, i.e. a gradient eluent. At the time 0 minutes, the eluent contains 100% of eluent A and 0% of eluent B. At 6 minutes, the eluent contains 100% of eluent A and 0% of eluent B. At 50 minutes, the eluent contains 65% of eluent A and 35% of eluent B.

The present invention also provides pharmaceutical composition comprising (S)-Pregabalin substantially free of (S)-Lactam and non-acidic pharmaceutically acceptable excipients.

The present invention further provides a process for preparing pharmaceutical formulation comprising mixing (S)-Pregabalin substantially free of (S)-Lactam and a non-acidic pharmaceutically acceptable carrier.

The present invention further provides the use of the (S)-Pregabalin substantially free of (S)-Lactam of the present invention for the manufacture of a pharmaceutical composition.

As used herein, the term "pharmaceutical compositions" includes tablets, pills, powders, liquids, suspensions, emulsions, granules, capsules, suppositories, or injection preparations. The pharmaceutical composition is preferably formulated without the use of acidic excipients. Pharmaceutical compositions containing the Pregabalin of the present invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers used include, but are not limited to, lactose, white sugar, sodium chloride, glucose, urea, starch, calcium carbonate, kaolin, crystalline cellulose, silicic acid, and the like. Binders used include, but are not limited to, water, ethanol, propanol, simple syrup, glucose solutions, starch solutions, gelatin solutions, carboxymethyl cellulose, shelac, methyl cellulose, potassium phosphate, polyvinylpyrrolidone, and the like. Disintegrating agents used include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, and the like. Disintegration inhibitors used include, but are not limited to, white sugar, stearin, coconut butter, hydrogenated oils, and the like. Absorption accelerators used include, but are not limited to, quaternary ammonium base, sodium laurylsulfate, and the like. Wetting agents used include, but are not limited to, glycerin, starch, and the like. Adsorbing agents used include, but are not limited to, starch, lactose, kaolin, bentonite, colloidal silicic acid, and the like. Lubricants used include, but are not limited to, purified talc, stearates, boric acid powder, polyethylene glycol, and the like. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, and esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of Pregabalin contained in a pharmaceutical composition for treating schizophrenia should be sufficient to treat, ameliorate, or reduce the symptoms associated with schizophrenia. Preferably, Pregabalin is present in an amount of about 1% to about 70% by weight, and more preferably from about 1% to about 30% by weight of the dose.

The pharmaceutical compositions of the invention may be administered in a variety of methods depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations may be administered intramuscularly, intracutaneously, subcutaneously or intraperitoneally. Suppositories may be administered into the rectum.

The dosage of a pharmaceutical composition for treating schizophrenia according to the invention will depend on the method of use, the age, sex, and condition of the patient. Preferably, Pregabalin is administered in an amount from about 0.1 mg/kg to about 10 mg/kg of body weight/day. More preferably, about 1 mg to 200 mg of Pregabalin may be contained in a dose.

The invention also encompasses methods of making a pharmaceutical formulation comprising combining Pregabalin, and a pharmaceutically acceptable excipient. As used herein, the term "pharmaceutical formulations" includes tablets, pills, powders, liquids, suspensions, solutions, emulsions, granules, capsules, suppositories, or injection preparations.

Having described the invention with reference to certain preferred embodiments, other embodiments will become apparent to one skilled in the art from consideration of the specification. The invention is further defined by reference to the following examples describing in detail the preparation of the compound of the present invention. It will be apparent to those skilled in the art that many modifications, both to materials and methods, may be practiced without departing from the scope of the invention.

EXAMPLES

The analysis for Lactam is done in Pregabalin crude, by the following method:

| | |
|---|---|
| HPLC | Inertsil ODS 3 V, 250*4.6 mm, 5µ. C.N 5020-01802 |
| Eluent A: | 80% 0.04 M $(NH_4)_2HPO_4$ adjusted to pH = 6.5 with $H_3PO_4$ |
| | 10% Acetonitrile |
| | 10% Methanol |
| Eluent B: | Acetonitrile |
| Stop time: | 50 min |
| Gradient of Eluent: | Time (min) / Eluent A (%) / Eluent B (%) |
| | 0 / 100 / 0 |
| | 6 / 100 / 0 |
| | 50 / 65 / 35 |
| Equilibration time: | 10 min |
| Flow: | 0.8 mL/min |
| Detector: | 210 nm |
| Injection volume: | 20 µL |
| Diluent: | Eluent A |
| Column temperature: | 25° C. |
| Autosampler temperature: | 5° C. |
| Detection Limit: | 0.002% |

Comparative Example

Analysis of a tablet of the 300 mg dose (expiry date: March 2007), was performed by dissolving the tablet in a mixture of water and methanol in a ratio of 1 to 1, to obtain a solution containing (S)-Pregabalin in a concentration of 6 mg/ml, followed by injecting to the HPLC apparatus. This analysis revealed that the tablet contains 0.02% area by HPLC of (S)-Lactam.

Example 1

Preparation of Pregabalin

A reactor (0.2L) was loaded with water (150 ml) and NaOH (32.3 gr) to obtain a solution. The solution was cooled to 5° C. and CMH (30 gr) was added. $Br_2$ (25.9 gr) was added dropwise (15 min) while keeping the temperature below 10° C. The mixture was heated to 60° C. for 15 min and then cooled to RT. Iso-butanol was added (90 ml) and then a solution of $H_2SO_4$ (66%) (32 ml) was added. The phases were separated, and the aqueous phase was extracted with iso-butanol (75 ml). $Bu_3N$ (32.6 ml) was added to the combined organic phases. The mixture was heated to dissolution and then was cooled to 2° C. and stirred for 1.5 h, to induce precipitation. The precipitate was filtered, washed and dried at 55° C. under vacuum, providing a 80.4% yield. Total purity: 99.7% area by HPLC, Lactam—0.005% area by HPLC.

Example 2

Preparation of Pregabalin

A reactor (0.2L) was loaded with water (62 ml) and NaOH (13.45 gr) to obtain a solution. The solution was cooled to 15° C. and $Br_2$ (25.9 gr) was added dropwise (15 min) while keeping the temperature below 10° C. After 10 min CMH (12.5 gr) was added. The mixture was heated to 60° C. for 15 min and then cooled to RT. Iso-butanol (62 ml) and then a solution of $H_2SO_4$ (66%) (32 ml) was added. The phases were separated, and the aqueous phase was extracted with Iso-butanol (31 ml). To the combined organic phases water (28 ml) and then $Bu_3N$ (13 gr) were added. The mixture was heated to dissolution and then was cooled to 2° C., and stirred for 1 h to induce precipitaion. The precipitate was filtered, washed and dried at 55° C. under vacuum, providing a 73.5% yield. Total purity: 98.0% area by HPLC, Lactam—0.012% area by HPLC.

Example 3

Preparation of Pregabalin

A reactor (0.5L) was loaded with water (175 ml) and NaOH (37.6 gr) to obtain a solution. The solution was cooled to 10° C. and CMH (35 gr) was added. $Br_2$ (30.24 gr) was added dropwise during a period of 0.5 h. The mixture was heated to 60° C. for 15 min and then cooled to RT. The solution was seperated to 2 portions.

Half of first portion (equal to 5 gr of CMH) was stirred for 5 h at RT, then isobutanol (15 ml) and a solution of $H_2SO_4$ (66%) (5 ml) were added. The phases were separated, and the aqueous phase was extracted with iso-butanol (12 ml). $Bu_3N$ (5.2 gr) was added to the combined organic phases. The solution was cooled to 2° C., and stirred for 1.5 h to induce precipitaion. The precipitate was filtered, washed and dried at 55° C. under vacuum, providing S-Pregabalin with total purity of 99.3% area by HPLC, (S)-Lactam—0.011% area by HPLC.

The second portion was treated as follows:
Iso-butanol was added (75 ml) then a solution of $H_2SO_4$ (66%) (25 ml) was added. The phases were separated, and the aqueous phase was extracted with iso-butanol (62 ml). The solution was separeted again into two portions (portions A & B). An amount of portion A (equal to 5 gr of CMH) was stirred for 24 h at RT, $Bu_3N$ (2.6 gr) was added and the solution was cooled to 2° C., and stirred for 1.5 h to induce precipitaion. The precipitate was filtered, washed and dried at 55° C. under vacuum, providing (S)-Pregabalin with total purity of 99.07% area by HPLC, (S)-Lactam—0.013% area by HPLC.

An amount of portion A (equal to 5 gr of CMH) was stirred for 0.5 h at RT, $Bu_3N$ (2.6 gr) was added and the solution was cooled to RT, and stirred for 24 h to induce precipitaion. The precipitate was filtered, washed and dried at 55° C. under vacuum, providing S-Pregabalin with total purity of 99.67% area by HPLC, (S)-Lactam—no detection.

Example 4

Preparation of Pregabalin

A reactor (0.2 L) was loaded with water (150 ml) and NaOH (32.3 gr) to obtain a solution. The solution was cooled to 15° C. and CMH (30 gr) was added. $Br_2$ (25.9 gr) was added dropwise (15 min) while keeping the temperature below 20° C. The mixture was heated to 60° C. for 15 min and then cooled to RT. Iso-butanol was added (150 ml) and then a solution of $H_2SO_4$ (66%) (30 ml) was added. The phases were separated, and the aqueous phase was extracted with iso-butanol (75 ml). The combined organic phases were separated to 3 portions.

Into portion 1, $Bu_3N$ (10.4 ml) was added and the mixture was cooled to 2° C., and stirred for 2 h to induce precipitation. The precipitate was filtered, washed and dried at 55° C. under vacuum, providing S-Pregabalin with total purity 99.7% area by HPLC, (S)-Lactam—0.008% area by HPLC.

Into portion 3, Water (10 ml) and $Bu_3N$ (10.4 ml) were added. The mixture was cooled to 2° C., and stirred for 2 h to induce precipitation. The precipitate was filtered, washed and dried at 55° C. under vacuum, providing S-Pregabalin with total purity 99.7% area by HPLC, (S)-Lactam—0.005% area by HPLC.

Example 5

Preparation of Pregabalin

A reactor (0.1 L) was loaded with water (50 ml) and NaOH (10.8 gr) to obtain a solution. The solution was cooled to 15° C. and CMH (10 gr) was added. $Br_2$ (8.6 gr) was added dropwise (15 min) while keeping the temperature below 20° C. The mixture was heated to 60° C. for 15 min and then cooled to RT. Iso-butanol was added (60 ml) and then a solution of $H_2SO_4$ (66%) (10 ml) was added. The phases were separated, and the aqueous phase was extracted with iso-butanol (25 ml). To the combined organic phases $Bu_3N$ (9.9 gr) was added and the mixture was cooled to 2° C., and stirred for 2 h to include precipitation. The precipitate was filtered, washed and dried at 55° C. under vacuum, providing S-Pregabalin with total purity 99.88% area by HPLC, (S)-Lactam—0.007% area by HPLC.

Example 6

Preparation of Pregabalin

A reactor (0.5 L) was loaded with water (165 ml) and NaOH (35.5 gr) to obtain a solution. The solution was cooled to 15° C. and CMH (33 gr) was added. $Br_2$ (28.51 gr) was added dropwise (15 min) while keeping the temperature below 25° C. The mixture was heated to 60° C. for 15 min and then cooled to 15° C. Iso-butanol was added (100 ml) and then a solution of $H_2SO_4$ (66%) (33 ml) was added. The phases were separated, and the aqueous phase was extracted with iso-butanol (83 ml). To the combined organic phases $Bu_3N$ (34.2 gr) was added and the mixture was cooled to 2° C., and stirred for 2 h to induce precipitation. The precipitate was filtered, washed and dried at 55° C. under vacuum, providing S-Pregabalin with total purity 99.86% area by HPLC, (S)-Lactam—no detection by HPLC.

Example 7

Preparation of Pregabalin

A reactor (0.1 L) was loaded with water (50 ml) and NaOH (10.8 gr) to obtain a solution. The solution was cooled to 15° C. and CMH (10 gr) was added. $Br_2$ (8.6 gr) was added dropwise (15 min) while keeping the temperature below 20° C. The mixture was heated to 60° C. for 15 min and then cooled to RT. Iso-butanol was added (30 ml) and then a solution of $H_2SO_4$ (66%) (10 ml) was added. The phases were separated, and the aqueous phase was extracted with iso-butanol (25 ml). To the combined organic phases water (16.5 ml) and $Bu_3N$ (10.4 gr) were added. The mixture was cooled to 2° C., and stirred for 2 h to induce precipitation. The precipitate was filtered, washed and dried at 55° C. under vacuum, providing Pregabalin with total purity 99.3% area by HPLC, Lactam—0.002% area by HPLC.

Example 8

Preparation of Pregabalin

A reactor (0.1 L) was loaded with water (50 ml) and NaOH (10.8 gr) to obtain a solution. The solution was cooled to 15° C. and CMH (10 gr) was added. $Br_2$ (8.6 gr) was added dropwise (15 min) while keeping the temperature below 20° C. The mixture was heated to 60° C. for 15 min and then cooled to RT. Iso-butanol was added (50 ml) and then a solution of $H_2SO_4$ (66%) (10 ml) was added. The phases were separated, and the aqueous phase was extracted with iso-butanol (25 ml). To the combined organic phases water (22.4 ml) and $Bu_3N$ (10.4 gr) were added. The mixture was cooled to 2° C., and stirred for 2 h to induce precipitation. The precipitate was filtered, washed and dried at 55° C. under vacuum, providing Pregabalin with total purity 98.5% area by HPLC, Lactam—0.005% area by HPLC.

Example 9

Preparation of Pregabalin

A reactor (0.2 L) was loaded with water (125 ml) and NaOH (26.9 gr) to obtain a solution. The solution was cooled to 15° C. and CMH (10 gr) was added. $Br_2$ (8.6 gr) was added dropwise (15 min) while keeping the temperature below 20° C. The mixture was heated to 60° C. for 15 min and then cooled to RT. Iso-butanol was added (75 ml) and then a solution of $H_2SO_4$-66% (25 ml) was added. The phases were separated, and the aqueous phase was extracted with iso-butanol (65 ml). The combined organic phases were separated to 3 portions. To one portion $Bu_3N$ (8.5 gr) was added. The mixture was cooled −10° C., and stirred for 2 h to induce precipitation. The precipitate was filtered, washed and dried at 55° C. under vacuum, providing Pregabalin with total purity 99.3% area by HPLC, Lactam—0.008% area by HPLC.

Example 10

Iso-butanol is added (30 ml) to pregabalin or to a complex of pregabalin with $H_2SO_4$. Afterwards, water (16.5 ml) and $Bu_3N$ (10.4 gr) are added. The mixture is cooled to 2° C., and stirred for 2 h to induce precipitation. The precipitate is filtered, washed and dried at 55° C. under vacuum, providing Pregabalin with total purity 99.3% area by HPLC, Lactam—0.002% area by HPLC.

Example 11

Preparation of a Pharmaceutical Formulation Containing (S)-Pregabalin

The following material is used for the preparation of Pregabalin tablet formulation:

| Ingredients | Amounts |
| --- | --- |
| Pregabalin | 125 g |
| Corn Starch NF | 200 g |
| Cellulose, Microcrystalline | 46 g |
| Sterotex Powder HM | 4 s |
| Purified Water | q.s. or 300 ml |

Combine corn starch, cellulose, and Pregabalin together in a mixer and mix for 2-4 minutes. Add water to this combination and mix for an addition 1-3 minutes. The resulting mix is spread on trays and dried in convection oven at 45-55° C. until a moisture level of 1 to 2% is obtained. The dried mix is then milled and added back to the mill mixture and the total is blended for additional 4-5 minutes. Compressed tables of 150 mg, 375 mg and 750 mg are 30 formed using appropriate punches from the total mix. The formulation is measured to contain less than 0.02% lactam.

The invention claimed is:

1. A process for obtaining Pregabalin substantially free of Lactam comprising:
   a) extracting an acidic mixture containing a complex of Pregabalin with a strong mineral acid, with a $C_{4-8}$ alcohol; and
   b) combining the organic phase with an organic base.

2. The process of claim 1, wherein the $C_{4-8}$ alcohol is selected from the group consisting of: butanol, iso-butanol, 2-butanol, pentanol and iso-pentanol.

3. The process of claim 2, wherein the $C_{4-8}$ alcohol is isobutanol.

4. The process of claim 1, wherein the strong mineral acid is selected from the group consisting of: HCl, HBr, $H_3PO_4$, and $H_2SO_4$.

5. The process of claim 4, wherein the strong mineral acid is $H_2SO_4$.

6. The process of claim 1, wherein the organic base is selected from the group consisting of: primary amine, secondary amine, tertiary amine and aromatic amine.

7. The process of claim 6, wherein the primary amine, secondary amine and tertiary amine contain respectively one, two, or three $C_1$ to $C_6$ alkyls.

8. The process of claim 7, wherein the primary amine, secondary amine and tertiary amine contain respectively one, two, or three $C_1$ to $C_4$ alkyls.

9. The process of claim 6, wherein the aromatic amine is pyridine.

10. The process of claim 6, wherein the organic base is secondary amine or tertiary amine.

11. The process of claim 10, wherein the secondary amine or tertiary amine contain respectively two or three $C_1$ to $C_6$ alkyls.

12. The process of claim 11, wherein the secondary amine or tertiary amine contain respectively two or three $C_1$ to $C_4$ alkyls.

13. The process of claim 12, wherein the secondary amine or tertiary amine is tertiary amine containing three $C_1$ to $C_4$ alkyls.

14. The process of claim 12, wherein the secondary amine is either diisopropylamine or dipropylamine.

15. The process of claim 13, wherein the $C_1$ to $C_4$ alkyl is butyl or ethyl.

16. The process of claim 15, wherein the $C_1$ to $C_4$ alkyl is butyl.

17. The process of claim 1, wherein a precipitate of Pregabalin is obtained.

18. The process of claim 17, further comprising recovering the precipitate of Pregabalin.

19. The process of claim 18, wherein the recovery includes cooling, filtering and drying.

20. The process of claim 1, wherein the Pregabalin obtained is substantially free of Lactam.

21. The process of claim 20, wherein the Pregabalin obtained contains less than 0.015% area by HPLC of Lactam.

22. The process of claim 20, wherein the Pregabalin obtained contains less than 0.01% area by HPLC of Lactam.

23. The process of claim 20, wherein the Pregabalin obtained contains less than 0.005% area by HPLC of Lactam.

24. The process of claim 1, wherein said Pregabalin is (S)-Pregabalin and said Lactam is (S)-Lactam.

25. The process of claim 21, wherein said Pregabalin is (S)-Pregabalin and said Lactam is (S)-Lactam.

26. The process of claim 22, wherein said Pregabalin is (S)-Pregabalin and said Lactam is (S)-Lactam.

27. The process of claim 23, wherein said Pregabalin is (S)-Pregabalin and said Lactam is (S)-Lactam.

* * * * *